United States Patent [19]

Phillips et al.

[11] 4,047,532
[45] Sept. 13, 1977

[54] VACUUM FORCEP AND METHOD OF USING SAME

[76] Inventors: Jack L. Phillips, 4929 Bancroft Drive; Timothy E. Dickinson, 9458 Showplace Drive, both of, La Mesa, Calif. 92041

[21] Appl. No.: 570,016

[22] Filed: Apr. 21, 1975

[51] Int. Cl.² .................... A61F 9/00; A61B 17/00
[52] U.S. Cl. ........................... 128/303 R; 294/64 R
[58] Field of Search ............... 128/303 R; 294/64 A, 294/64 R

[56] References Cited

U.S. PATENT DOCUMENTS

| 2,224,575 | 12/1940 | Montalvo-Guenard | 128/303 R |
|---|---|---|---|
| 2,379,629 | 7/1945 | Eweson | 128/303 R |
| 2,555,076 | 5/1951 | Crossley | 128/303 R |
| 3,074,407 | 1/1963 | Moon et al. | 128/303 R |
| 3,589,363 | 6/1971 | Banko et al. | 128/276 |
| 3,608,946 | 9/1971 | Erickson et al. | 294/64 R |
| 3,913,148 | 10/1975 | Potthast | 128/303 R X |
| 3,926,192 | 12/1975 | Van Maren | 128/276 X |

*Primary Examiner*—Channing L. Pace
*Attorney, Agent, or Firm*—Charles H. Schwartz

[57] ABSTRACT

A suction forcep used to grasp an artificial lens and implant same in the human eye following cataract surgery comprises a smooth, flexible suction head mounted on a stem-like handle connected to a controlled vacuum source, the lens being held against the suction head by a partial vacuum maintained therein while the lens is positioned beneath the partially withdrawn cornea of an eye in alignment with the pupil thereof.

13 Claims, 10 Drawing Figures

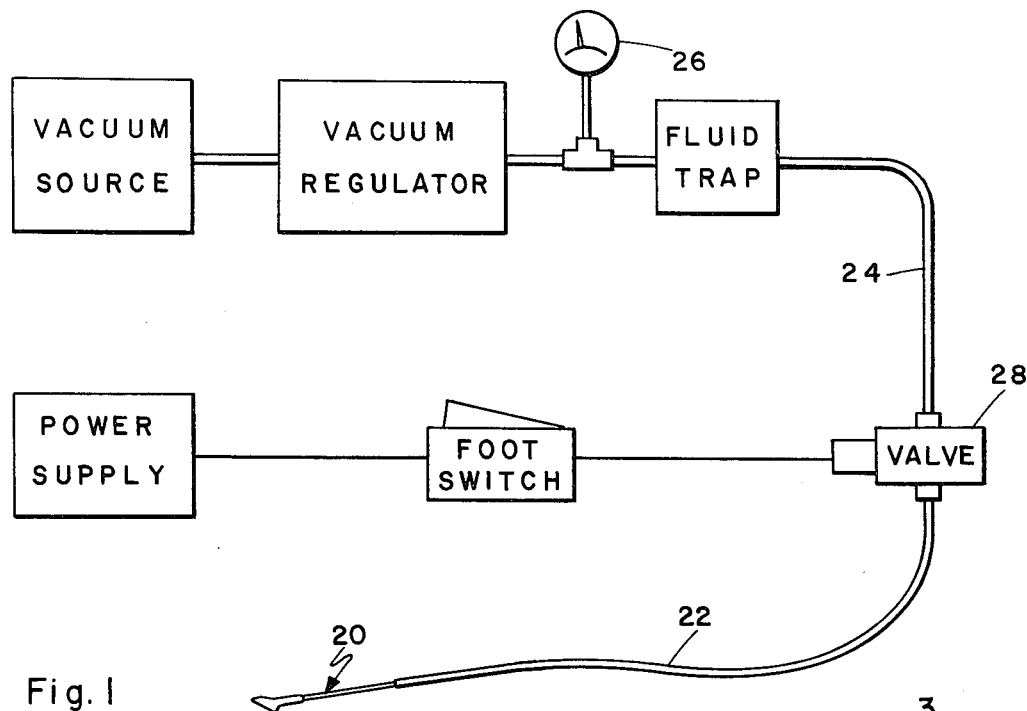
Fig. 1
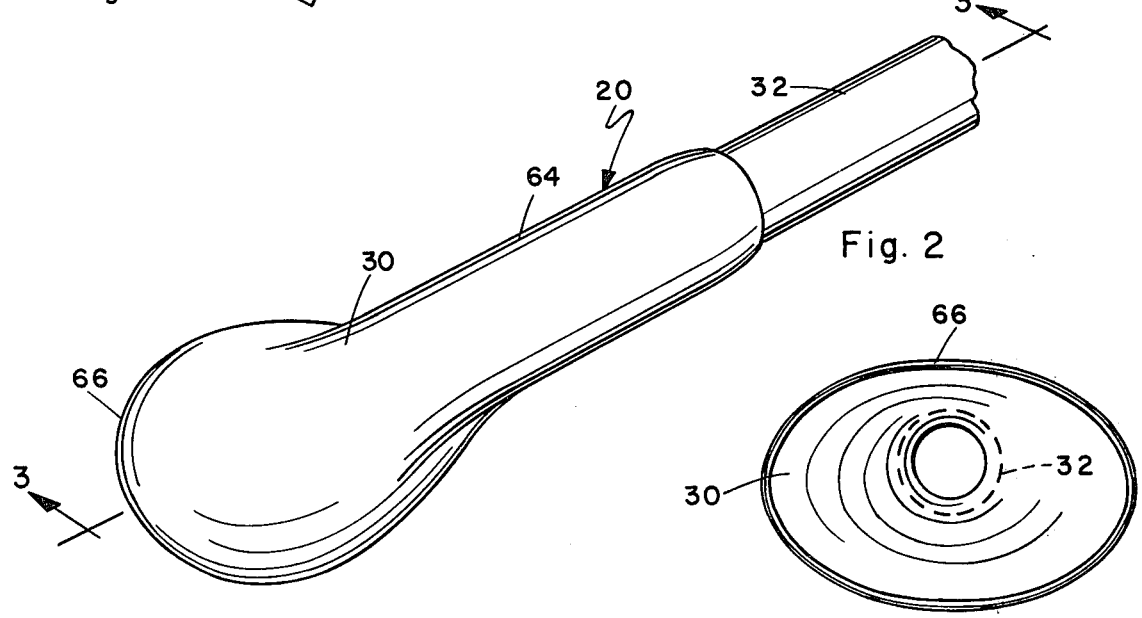
Fig. 2
Fig. 4
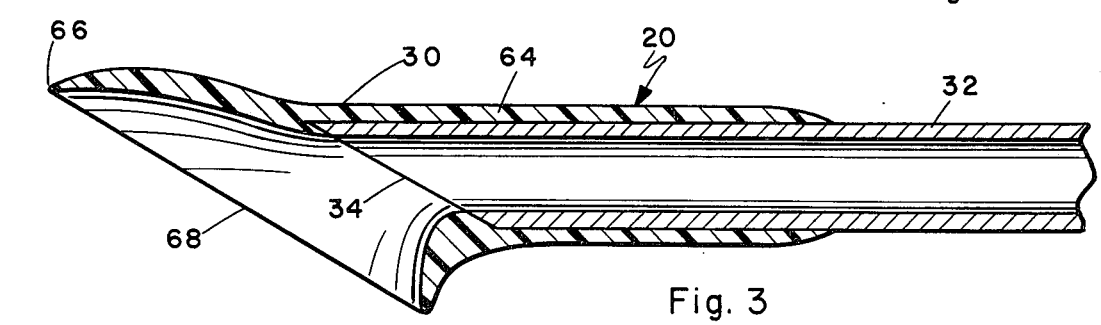
Fig. 3

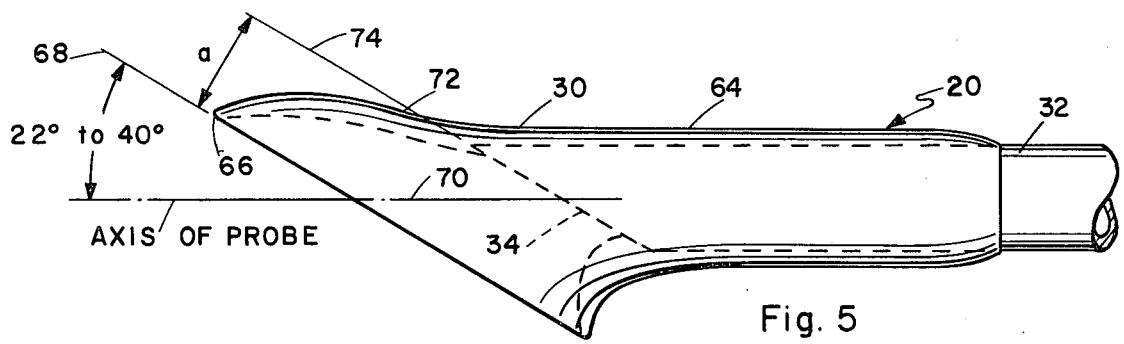
Fig. 5
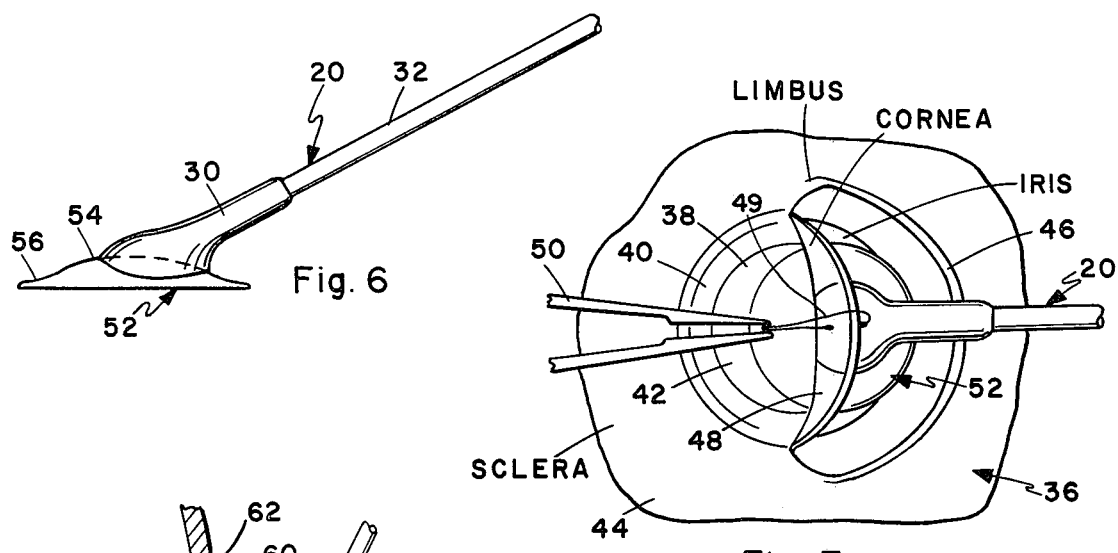
Fig. 6
Fig. 7
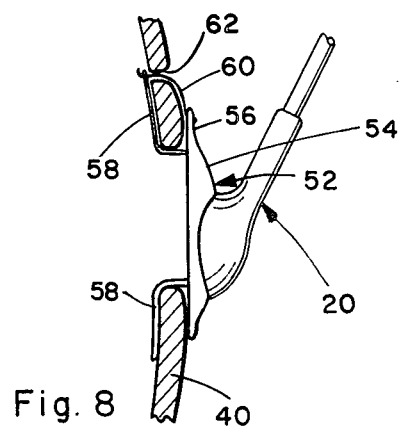
Fig. 8
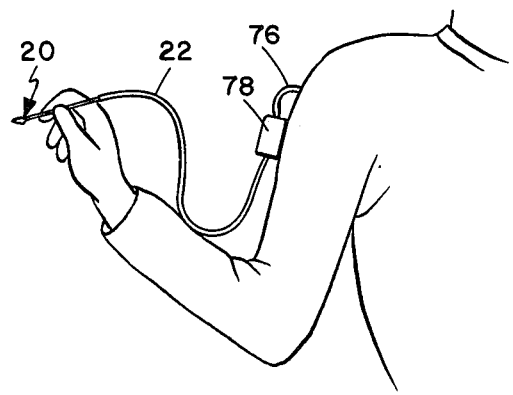
Fig. 10
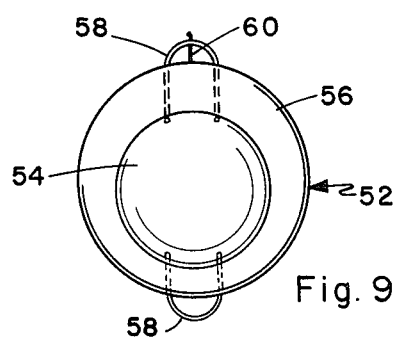
Fig. 9

VACUUM FORCEP AND METHOD OF USING SAME

BACKGROUND OF THE INVENTION

The invention is in the field of cataract surgery and more particularly relates to a means and method of implanting an artificial lens in the eye subsequent to the removal of the natural lens which has become clouded with cataracts.

Cataract surgery is a routine operation generally performed on the elderly and involves opening the eye along a peripheral portion of the cornea, removing the clouded natural lens, and suturing the cornea back to the eye. Although the basic cataract operation has been performed for years, a variety of improved techniques for removing the natural lens have been developed in recent years. However, until very recently, the lensless eyes of many of the aphakic patients were not completely correctable and the patient would be required to wear extremely thick glasses or exend contact lenses to achieve that degree of correction which was possible.

Very recently a technique has been developed wherein during the cataract operation and subsequent to the removal of the natural lens an artificial lens is inserted into the eye itself beneath the cornea thereof prior to closing the cornea. The artificial lens, which according to current practices is sutured or otherwise attached directly to the iris, in many cases effects the nearly complete correction of the eye without requiring external correction. However, the lenses are currently being held during implant procedure with slightly modified forceps, which is a somewhat awkward procedure and risks scratching or marring the lens, as well as injury to the eye when the forceps are released due to the hand motion required in the limited sphere of operation to release the lens.

SUMMARY OF THE INVENTION

The present invention is a vacuum forcep used to pick up and hold the lens preparatory to the above described implant procedure, the lens being held on a small resilient suction head connected through an integral stem and flexible tubing to a controlled vacuum source. The smooth suction head is the only part of the apparatus that enters the eye or touches the lens so that injury to the eye or the lens is minimal, and subsequent to properly positioning the lens in the eye, release of the lens by dissipating the suction in the suction head is accomplished by operating a foot-operated control valve or other remote control station so that no motion is required near the eye.

BRIEF DESCRIPTION OF THE DRAWINGS

FIG. 1 is a diagram of the system for operating the tool;

FIG. 2 is an enlarged perspective view of the tool tip;

FIG. 3 is a sectional view taken on line 3—3 of FIG. 2;

FIG. 4 is an end view of the tool as taken from the left hand end of FIG. 3;

FIG. 5 is a side elevation view of the tool tip, illustrating the configuration;

FIG. 6 illustrates the tool holding a lens; and

FIG. 7 illustrates the tool in use in inserting a lens into an eye; and

FIG. 8 is a vertical section through the iris showing the lens held in place by the probe and lens loops.

FIG. 9 is a front elevation view of the lens showing the attaching loop structure;

FIG. 10 is a diagrammatic view showing the arm of an operating surgeon with a tube junction box attached to his upper sleeve.

DETAILED DESCRIPTION OF THE PREFERRED EMBODIMENT

The invention is presented in diagrammatic and self-explanatory fashion in FIG. 1, wherein a vacuum forcep probe 20 is connected through flexible tubing 22 to a vacuum system comprising a conduit 24 connected to a vacuum source, the vacuum level being controlled by a regulator as shown. A gauge 26, and fluid trap are provided in the line for obvious reasons, and a solenoid-operated valve 28, having a power supply and being controlled by a foot switch, alternatively connects the flexible tubing 22 either to the conduit 24, or directly to the atmosphere or a source of slightly positive pressure, to abate the vacuum in the forcep. The vacuum system shown is exemplary and subject to engineering modifications, the foot switch for example being replaceable by any suitable remote control device for the venting valve 28, or this valve being deleted entirely in favor of a remote vacuum abatement capability operating the vacuum regulator directly.

The forcep probe 20 comprises a suction head 30 constructed to fall within fairly definite design parameters, as described below, and a hollow stem 32 integral with the suction head and connected to the flexible tubing. The stem should be no greater than 3 millimeters in outside diameter, at least at the suction head end, and may be composed of stainless steel, plastic, or other material. The stem need not be completely rigid, and a fairly flexible form may be used in conjunction with a rigid sheath-like handle to support the stem near the suction head, although a simple stainless steel tube beveled as at 34 has been found quite satisfactory in this capacity.

In order to understand the structural limitations of the suction head and adjoining stem, it is necessary to understand basic eye anatomy and the nature of the implant operation. A portion of a human eye 36 is shown in FIG. 7 having a pupil 38 surrounded by the iris 40 and normally covered by the cornea 42. The cornea of the eye in FIG. 7 has been separated from the sclera 44 at the limbus or marginal area of the cornea, creating an arcuate wound area 46 describing between 160° and 180° of arc. The portion 48 of the cornea which has been severed from engaged with a suture 49 and withdrawn from the wound and held in this withdrawn position by forceps 50 so that an opening into the pupil and iris region of the eye is created.

After the opening has been created, the natural lens of the eye is removed, this procedure not being illustrated inasmuch as it is not part of the instant invention. Subsequent to the removal operation, an artificial lens 52 is positioned on the suction head and retained by a partial vacuum while the surgeon grasps the stem 32 and inserts the lens in the eye, as shown in FIG. 7. The lens, which would ordinarily be composed of methyl methacrylate, has a central optical area 54 and a surrounding haptic portion 56 which according to conventional design contacts the iris 40 and is secured thereto by two radially extended posterior loops 58 one of which is engaged at the distal end by a platinum wire 60 which extends from the edge of the lens through a hole 62 pierced in the iris. Other types of lenses are used which are connected differently than the lens shown in the drawings, but with one exception mentioned below they need not be detailed herein.

Subsequent to the positioning of the lens, it is released either before or after attachment to the iris is consummated, depending on the particular procedure and lens type used. Release is effected by operating the foot switch to dissipate the vacuum in the head, so that no movement is necessary in the vicinity of the eye. The vacuum release switch could be installed in the probe itself, although a sophisticated design would be called for to provide the needed sensitivity without incurring a substantial risk of accidentally tripping the switch at an inopportune movement.

The suction head of the probe must be made in accordance with certain specifications to function in the intended capacity. The material from which it is made must be compatible with various media encountered in the surgical environment, such as salt solutions and sterilizing gases, so that no chemical breakdown or dissolution occurs during use, and it is highly desirable that the material be transparent to aid the surgeon during the implant operation. These requirements can be met by a medical grade elastomer which is medically free of foreign particulate matter and living organisms, a Dow-Corning substance marked under the trademark SILASTIC having been found suitable. A special process is used to mold the head directly on the stem so that a shank portion 64 is formed around the stem, the shank diverging into a generally annular and somewhat radially extended lip 66 of diameter no greater than the artificial lens to be implanted and preferably somewhat less. The lip is thin and fairly flexible, and has a slight frictional quality permitting the firm grasping of the lens by the head when a vacuum level of approximately 10 to 20 inches of mercury is reached. In practice, a lip diameter of about 4 millimeters has been found to be close to optimal, and absolute maximum diameter of 8 millimeters is prescribed due to the size limitations of the eye.

The lip 66 defines a face of the suction head, indicated at 68, this face defining an angle with the axis 70 which is no greater than 60° and preferably falls between the limits of 22° and 40°. Some angle is needed because the incision in the eye is generally made above the pupil and brow clearance is required, but an angle greater than necessary would require that a larger than desireable incision be made in the cornea. cornea clearance also dictates that the distance between the face of the suction head and the rear surface 72 be no more than 4 millimeters as measured at a between the plane 68 and the line 74. The rear surface will not normally come into contact with the cornea but should be smooth and roundly contoured in any event.

In one arrangement of the device, the vacuum source is connected by a flexible tube 76 to a tube junction box 78 which is attachable to the upper sleeve of the operating surgeon as shown in FIG. 10. The flexible tubing 22 is attached to the junction box as shown, and follows the surgeon's arm down to the forcep probe 20 so that the tubing does not dangle in the field of operation. This arrangement also permits the forcep probe and connecting tubing to be provided in a sterilized package so that the tubing can be attached to the junction box in sterile condition, as is required in the field of operation, and detached and discarded subsequent to the operation. The tubing should be as lightweight and flexible as possible to minimize interference with the operation.

Although in the procedure described the lens is attached to the front of the iris, experimentation has been done on lens implants posteriorly of the iris. In this procedure, it is clear that the use of conventional forceps would be impractical if not impossible, since the holding implement would have to grip the front surface rather than the edges of the lens, and the vacuum forcep would prove to be an effective and virtually essential tool for the successful completion of the operation.

We claim:

1. A vacuum forcep for attachment to a controlled variable vacuum source for temporarily holding an artificial lens and inserting the lens beneath the partially withdrawn cornea of the human eye and adjacent the iris, the forcep including
    an elongated essentially straight hollow stem having a longitudinal axis, the exterior of the stem defining a handle for manipulation by an operating surgeon, the stem being essentially rigid;
    a flexible suction head having a shank portion disposed on one end of the stem and defining a cavity communicating with the hollow stem;
    the suction head having a hollow face extending from the shank portion and communicating with the cavity in the shank portion and comprising a yielding, generally radially outwardly extending substantially annular lip of outside diameter less than that of the human cornea and a radial cross-sectional area greater than that of the shank portion, the face defining an angle greater than 0° and less than 60° with the extension of the axis of the stem past the face; and
    the suction head having a smoothly contoured rear surface on the side generally opposite from the face, whereby an artificial lens may be vacuum grasped by the face of the suction head, positioned with the eye beneath a partially withdrawn cornea and maintained in place until release is affected by abating vacuum in the head.

2. The vacuum forcep of claim 1 wherein the stem has an annular end wall and the cavity on the head completely embraces the end wall such that the suction head joins the stem at a position at least as radially inward as the end wall to eliminate any possibility of contact of the end wall with a lens grasped by the suction head.

3. The vacuum forcep of claim 1 wherein the extension of the axis passes through the annular lip, whereby rotational adjustment of the stem in the operation procedure affects the rotation of the head about the axis of the stem with little accompanying translational motion of the head.

4. The vacuum forcep of claim 1 wherein the extension of the axis of the stem passes through the central region of the area circumscribed by the annular lip.

5. The vacuum forcep of claim 1 wherein the head flares outwardly at an intermediate position to define the lip and the cavity in the head flares outwardly in accordance with the outward flaring of the head.

6. The vacuum forcep of claim 1 wherein the flexible suction head is molded and has one edge extending beyond an opposite edge of the suction head such that a somewhat laterally directed and radially asymmetric suction cavity is defined by the suction head and the rear surface of the suction head joining the one edge and the shank is continuous and protuberance free to permit the unhindered passage of the forcep through a cut of minimal extent made in the lumbus region of the eye.

7. The vacuum forcep of claim 1 wherein the suction head is composed of a soft, medical grade transparent elastomer.

8. The vacuum forcep of claim 1 wherein the suction head comprises a resilient material molded onto the end of the rigid stem.

9. The vacuum forcep of claim 1 wherein the angle between the face of the head and the extension of the axis of the stem past the face of the head is between 22° and 40°.

10. The vacuum forcep of claim 1 wherein the stem is rigid and cylindrical and includes a length of flexible tubing connected to the stem on the remote end thereof from the suction head, the tubing, stem, and suction head forming a disposable unit.

11. The vacuum forcep of claim 1 wherein the controlled variable vacuum source is connected to the hollow stem for providing a vacuum at the suction head for vacuum gripping an artificial lens by the face of the suction head to position the artificial lens with the eye beneath a partially withdrawn cornea and to maintain the artificial lens in place until release is effected by abating the vacuum from the controlled source.

12. The vacuum forcep of claim 11 wherein the controlled vacuum source includes means remote from the suction head and stem to abate the vacuum pressure.

13. The vacuum forcep of claim 12 wherein the pressure abatement means comprises a valve operable to vent the suction head and stem to atmospheric pressure.

* * * * *